United States Patent
Haibach

(10) Patent No.: US 10,869,983 B2
(45) Date of Patent: Dec. 22, 2020

(54) OVERMOLDED SWIVEL WITH ANGULAR INTERLOCK

(71) Applicant: KONINKLIJKE PHILIPS N.V., Eindhoven (NL)

(72) Inventor: Richard Thomas Haibach, Verona, PA (US)

(73) Assignee: Koninklijke Philips N.V., Eindhoven (NL)

( * ) Notice: Subject to any disclaimer, the term of this patent is extended or adjusted under 35 U.S.C. 154(b) by 1366 days.

(21) Appl. No.: 14/933,276

(22) Filed: Nov. 5, 2015

(65) Prior Publication Data

US 2016/0228667 A1 Aug. 11, 2016

Related U.S. Application Data

(60) Provisional application No. 62/076,707, filed on Nov. 7, 2014.

(51) Int. Cl.
*A61M 16/08* (2006.01)
*B29C 45/14* (2006.01)
(Continued)

(52) U.S. Cl.
CPC .... *A61M 16/0816* (2013.01); *A61M 16/0825* (2014.02); *B29C 45/14598* (2013.01);
(Continued)

(58) Field of Classification Search
CPC .......... A61M 16/0816; A61M 16/0825; A61M 16/0875; A61M 2207/00; A61M 2207/10;
(Continued)

(56) References Cited

U.S. PATENT DOCUMENTS

| 4,917,846 A | * | 4/1990 | Takase | B29C 33/52 249/59 |
| 5,042,153 A | * | 8/1991 | Imao | B29C 39/10 29/527.2 |

(Continued)

FOREIGN PATENT DOCUMENTS

WO WO-2012143819 A1 * 10/2012 ........ A61M 16/0816

*Primary Examiner* — Colin W Stuart
*Assistant Examiner* — Douglas Y Sul
(74) *Attorney, Agent, or Firm* — Michael W. Haas

(57) ABSTRACT

An angular interlock for a swivel feature formed using injection molding techniques is described herein. In one exemplary embodiment, the swivel feature is used for a conduit for delivering breathing therapy to a patient, and includes an outer swivel component and an inner swivel component formed using a two-shot molding technique. The outer swivel component is formed first out of a material, such as polycarbonate, having a low shrink rate, whereas the inner swivel component is formed of a material, such as polypropylene, having a high shrink rate. The material for the inner swivel component is injected into the formed outer swivel component and allowed to cool, creating a clearance. The outer swivel component includes an angular interlock protrusion that allows the inner swivel component to be formed without creating an interface about the angular interlock protrusion, which typically occurs with standard rectangular interlocks.

21 Claims, 6 Drawing Sheets

(51) Int. Cl.
*A61M 16/06*    (2006.01)
*B29K 23/00*    (2006.01)
*B29K 669/00*   (2006.01)

(52) U.S. Cl.
CPC ... *B29C 45/14754* (2013.01); *A61M 16/0633* (2014.02); *A61M 2207/00* (2013.01); *B29C 2045/14762* (2013.01); *B29K 2023/12* (2013.01); *B29K 2669/00* (2013.01)

(58) Field of Classification Search
CPC .. A61M 39/00; A61M 39/10; A61M 39/1055; F16L 27/08–0865; B29K 45/14754; B29K 45/14598
USPC .................................. 264/242; 285/272, 278
See application file for complete search history.

(56) References Cited

U.S. PATENT DOCUMENTS

| | | | |
|---|---|---|---|
| 6,702,469 B1* | 3/2004 | Taniguchi | B29C 45/14754 384/418 |
| 7,108,293 B2 | 9/2006 | Van Der Meijden | |
| 8,806,920 B2 | 8/2014 | Blekher | |
| 2002/0128607 A1* | 9/2002 | Haury | A61M 5/14546 604/187 |
| 2004/0243072 A1 | 12/2004 | Hansen | |
| 2005/0077726 A1* | 4/2005 | White | A61M 16/08 285/147.1 |
| 2009/0143767 A1 | 6/2009 | Fentress | |
| 2014/0150897 A1* | 6/2014 | Ashiba | F16F 9/3485 137/343 |

* cited by examiner

US 10,869,983 B2

OVERMOLDED SWIVEL WITH ANGULAR INTERLOCK

CROSS-REFERENCE TO RELATED APPLICATIONS

This patent application claims the priority benefit under 35 U.S.C. § 119(e) of U.S. Provisional Application No. 62/076,707, filed on Nov. 7, 2014, the contents of which are herein incorporated by reference.

BACKGROUND OF THE INVENTION

1. Field of the Invention

The present invention generally relates to a swivel feature for a breathing therapy conduit that includes an angular interlock. In particular, the angular interlock used for the swivel feature allows for injection molding techniques to be used without compromising the swivel feature's ability to rotate as a result of shrinkage of an injected material.

2. Description of the Related Art

Continuous positive airway pressure ("CPAP") therapy is an extremely beneficial form of breathing therapy for patients suffering from sleep apnea or other respiratory issues. The breathing therapy is typically provided to a patient via patient interface device, such as a mask, which receives air and/or gas from a pressure generating device. The pressure generating device is coupled to the patient interface device by means of a hose or conduit. In order to effectively deliver the therapy throughout the duration of the treatment regime, the conduit should have a strong seal maintained along the entire length of the conduit so that the breathing therapy does not exit the conduit prior to delivery to the patient interface device and thus, the patient. Another important characteristic of the conduit is that it should be capable of freely rotating about the patient interface device or at certain junction points where pieces of conduit couple together. If the conduit is not capable of rotating freely, the conduit is more likely to deform and break, as well as causing discomfort to the patient.

Most swivel features for breathing therapy conduits are formed by "snapping" or fitting two separate pre-formed plastic pieces together. This technique, however, has inherit drawbacks in that the two separate components will have some form of unwanted or unintentional spacing between them. This spacing allows for the two components to be fitted together; however it also will lead to a poor seal between the two parts, and thus leakage if too large.

Injection molding, such as two shot molding or overmolding, is a possible solution to this problem as the shrink rates of the materials used for molding allow the spacing to be controlled and minimized. Plastics, such as polypropylene, have high shrinkage rates. Typically, for a uniform material having a constant thickness, the shrinkage rate is the same in both the x and y direction. However, swivel features typically use rectangular interlocks to secure a first molded component with a second molded component.

Therefore, if two-shot injection molding were to be used to form rectangular interlocks commonly used for swivel components, the injected material would shrink away from the inner surface of the outer mold, as well as also shrinking inwards along the longitudinal axis of the swivel component creating an undesirable and detrimental interference or bind about the rectangular interlocks. This problem is illustrated schematically in FIGS. 1-3.

FIG. 1 is a schematic illustration of a cross-sectional view of a prior art outer swivel component 210 of a prior art swivel feature 200 including a rectangular interlock protrusion 212. Swivel feature 200 initially (e.g., prior to injection molding of an inner swivel component 220) includes outer swivel component 210 having rectangular interlock protrusion 212. Outer swivel component 210 and rectangular interlock protrusion 212 are substantially annular. Outer swivel component 210 has a first diameter 200D1, which is substantially constant about an inner surface 206 of outer swivel component 210. Furthermore, rectangular interlock protrusion 212 has a second diameter 200D2, which is also substantially constant about inner surface 206 of outer swivel component 210.

Rectangular interlock protrusion 212 extends out along the radial axis from inner surface 206 of outer swivel component 210 by a distance 212D1, which is equal to the difference between first diameter 200D1 and second diameter 200D2. In the illustrated embodiment, rectangular interlock protrusion 212 extends outwards from inner surface 206 such that it forms an angle 212A1 between itself and inner surface 206. In the illustrated embodiment, angle 212A1 is approximately 90-degrees, however an angle of approximately 105-degrees or less will also generally lead to interference issues with injection molding techniques as will be described below. Furthermore, rectangular interlock protrusion 212 of outer swivel component 210 has a width 212L1 along the longitudinal axis of outer swivel component 210.

FIG. 2 is a schematic illustration of a side view of outer swivel component 210 of FIG. 1 having an inner swivel component material 202 injected therein in accordance with an injection molding process. Inner swivel component material 202, such as a plastic having a high shrink rate (e.g., polypropylene), is injected into an inner cavity formed by inner surface 206 of outer swivel component 210. In the illustrated embodiment, inner swivel component material 202 is injected substantially evenly about inner surface 206 such that it "extends" uniformly along the y-axis by a distance 220Y1, as well as uniformly about the x-axis of inner surface 206 of outer swivel component 210. Furthermore, material 202 may permeate throughout the entire inner cavity formed by inner surface 206 of outer swivel component 210 such that distance 220Y1 equals first diameter 200D1 of FIG. 4. A split-ring washer or other component may be inserted along the longitudinal axis of swivel 200 such that inner swivel component material 202 will extend uniformly from inner surface 206 of outer swivel component 210 and along the longitudinal axis of outer swivel component 210.

Inner swivel component material 202 is injected into swivel 200 at a substantially high temperature such that inner swivel component material 202 does not harden and/or set. After inner swivel component material 202 is injected, it is allowed to cool for a defined period of time. As cooling occurs, inner swivel component material 202 shrinks at a specific shrinkage rate defined by the chemical composition of inner swivel component material 202.

FIG. 3 is a schematic illustration of a cross-sectional side view of a portion of outer swivel component 210 of FIG. 2 after inner swivel component material 202 has cooled and shrunk. Swivel feature 200 of FIG. 6 shows a top portion of swivel feature 200 of FIG. 2 after cooling has occurred for illustrative purposes only. As inner swivel component material 202 shrinks, inner swivel component 220 forms, and inner swivel component material 202 shrinks in both the x and y-axes at a substantially similar rate.

Inner swivel component 220 has a thickness 220Y2 along the y-axes, or the radial axis. Thickness 220Y2 is smaller than thickness 220Y1 (e.g., the initial thickness of inner swivel component material 202 when injected), and thus a clearance 230 is formed between inner swivel component 220 and inner surface 206 of outer swivel component 210. In the illustrated embodiment, clearance 230 has a thickness 220Y3, which corresponds to the difference between distance 220Y1 and distance 220Y2 (e.g., the amount material 202 shrunk).

In the illustrated embodiment, inner swivel component material 202 would, in the absence of outer swivel component 210, shrink by a distance 222X1 along the x-axis, or the longitudinal axis, when it cools as shown in FIG. 3. However, since rectangular interlock protrusion 212 has length 212L1, as injected inner swivel component material 202 cools and attempts to shrink, the material tightly abuts rectangular interlock protrusion 212 forming a coating around protrusion 212. Thus, unlike in the y-direction, where clearance 230 is formed due to the shrinkage along the y-axis, material 202 has nowhere to go along the x-axis because of rectangular protrusion 212 and thus causes an interference between inner swivel component 220 and rectangular interlock protrusion 212 of outer swivel component 210. The interference hinders inner swivel component 220 from properly rotating, or swiveling, within outer swivel component 210.

SUMMARY OF THE INVENTION

Accordingly, it is an objective of this invention to provide a swivel feature including an angular interlock. In one exemplary embodiment, a swivel feature for a conduit between a pressure generating device delivering breathing therapy to a patient and a patient interface device donned by the patient is provided. The swivel feature includes an outer swivel component that is substantially annular and includes an angular interlock protrusion extending radially inward from an inner surface of the outer swivel component. The swivel feature also includes an inner swivel component that is substantially annular and includes an angular interlock receiving portion that the angular interlock protrusion extends into. The angular interlock receiving portion is created after an inner swivel component material is injected into the outer swivel component and allowed to cool for a period of time. This creates a clearance along a radial axis between an outer surface of the inner swivel component and the inner surface of the outer swivel component, an a clearance along a longitudinal axis between both sides of the angular interlock protrusion and the angular interlock receiving portion.

DETAILED DESCRIPTION OF EXEMPLARY EMBODIMENTS

Figure 1:
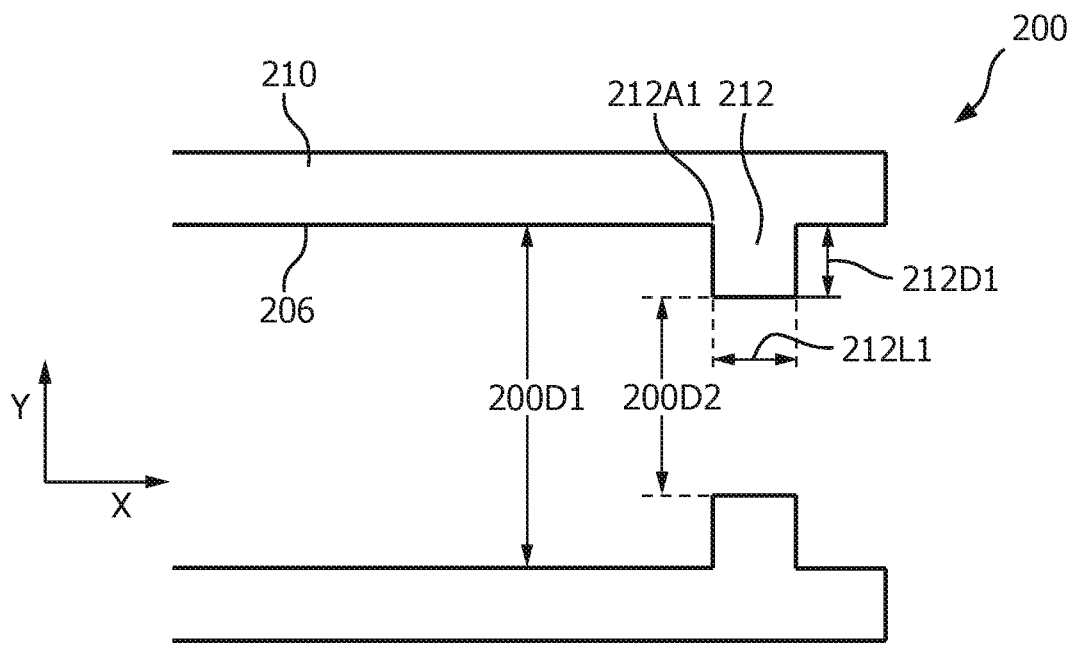
FIG. 1 is a schematic illustration of a cross-sectional view of a prior art outer swivel component of a prior art swivel feature including a rectangular interlock protrusion.

The present invention may take form in various components and arrangements of components, and in various techniques, methods, or procedures and arrangements of steps. The referenced drawings are only for the purpose of illustrated embodiments, and are not to be construed as limiting the present invention. Various inventive features are described below that can each be used independently of one another or in combination with other features. Furthermore, as used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" on another shall mean that the parts exert a force against one another either directly or through one or more intermediate parts or components. As employed herein, the term "number" shall mean one or an integer greater than one (e.g., a plurality).

As used herein, a "substantially fluid tight seal" means that two surfaces sealingly engage each other in a manner that substantially limits passage of fluid or gas between the two surfaces (e.g., no more than 5% passage). As used herein, the term "sealingly" or "sealed" in the context of an engagement, attachment or coupling means that two parts are coupled to one another with a substantially fluid tight seal.

Direction phrases used herein including, but not limited to, top, bottom, right, left, upper, lower, front, back, rear, and derivatives thereof, relate to the orientation of the elements shown in the drawings and are not limiting upon the claims unless expressly recited therein.

Figure 4:
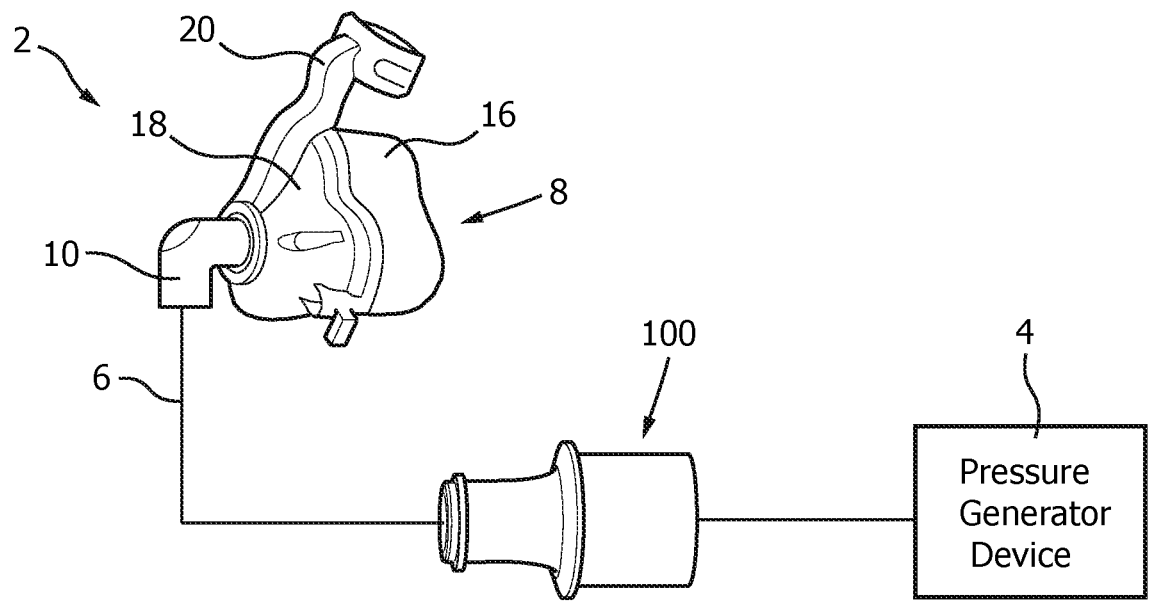
FIG. 4 is a schematic illustration of a system adapted to provide a regimen of respiratory therapy to a patient in accordance with various embodiments.

A system 2 adapted to provide a regimen of respiratory therapy to a patient according to one exemplary embodiment of the invention is generally shown in FIG. 4. System 2 includes a pressure generating device 4, a delivery conduit 6 coupled to pressure generating device 4 by a swivel feature 100 (described in greater detail herein), and a patient interface device 8 including an elbow conduit 10 coupled to delivery conduit 6. In one embodiment, swivel feature 100 may be coupled to a hose that couples to pressure generating device 4. In another embodiment, a hose couples to swivel feature 100 and patient interface device 8. However, persons of ordinary skill in the art will recognize that swivel feature 100 may be inserted at one or more positions within system 2, and the aforementioned is merely exemplary. Pressure generating device 4 is structured to generate a flow of breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, Pa.), and auto-titration pressure support devices. Delivery conduit 6 is structured to communicate the flow of breathing gas from pressure generating device 4 to patient interface device 8.

In the illustrated embodiment, patient interface 8 is a nasal/oral mask structured to cover the nose and mouth of the patient. However, any type of patient interface device 8, such as, without limitation, a nasal mask that covers the patient's nose, a nasal cushion having nasal prongs that are received within the patient's nares, or a full face mask that covers the patient's face, which facilitates the delivery of the flow of breathing gas to, and the removal of a flow of exhalation gas from, the airway of a patient may be used while remaining within the scope of the present invention. In the embodiment shown in FIG. 4, patient interface 8 includes a flexible cushion 16, a rigid or semi-rigid shell 18, and a forehead support 20. Straps (not shown) of a headgear component may be attached to shell 18 and forehead support 20 to secure patient interface device 8 to the patient's head. An opening in shell 18 to which elbow conduit 10 is coupled allows the flow of breathing gas from pressure generating device 4 to be communicated to an interior space defined by shell 18 and cushion 16, and then, to the airway of a patient. The opening in shell 18 also allows the flow of exhalation gas (from the airway of such a patient) to be communicated to a valve assembly 12 provided in, for example, elbow conduit 10.

Figure 5:
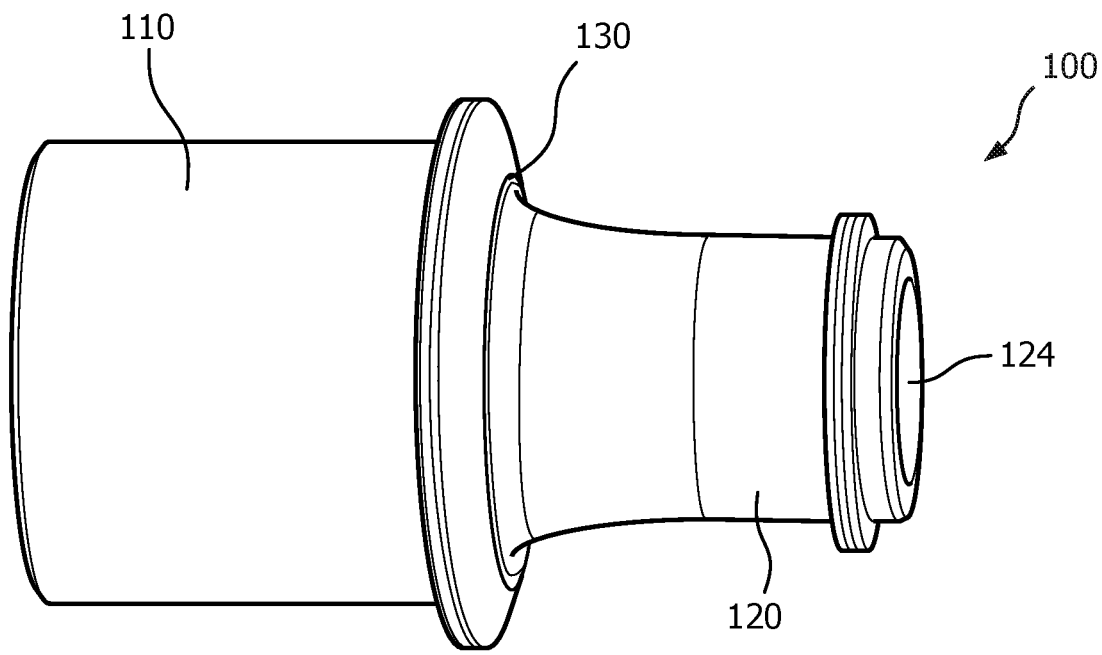
FIG. 5 is a schematic illustration of a side view of a swivel feature in accordance with various embodiments.
Figure 6:
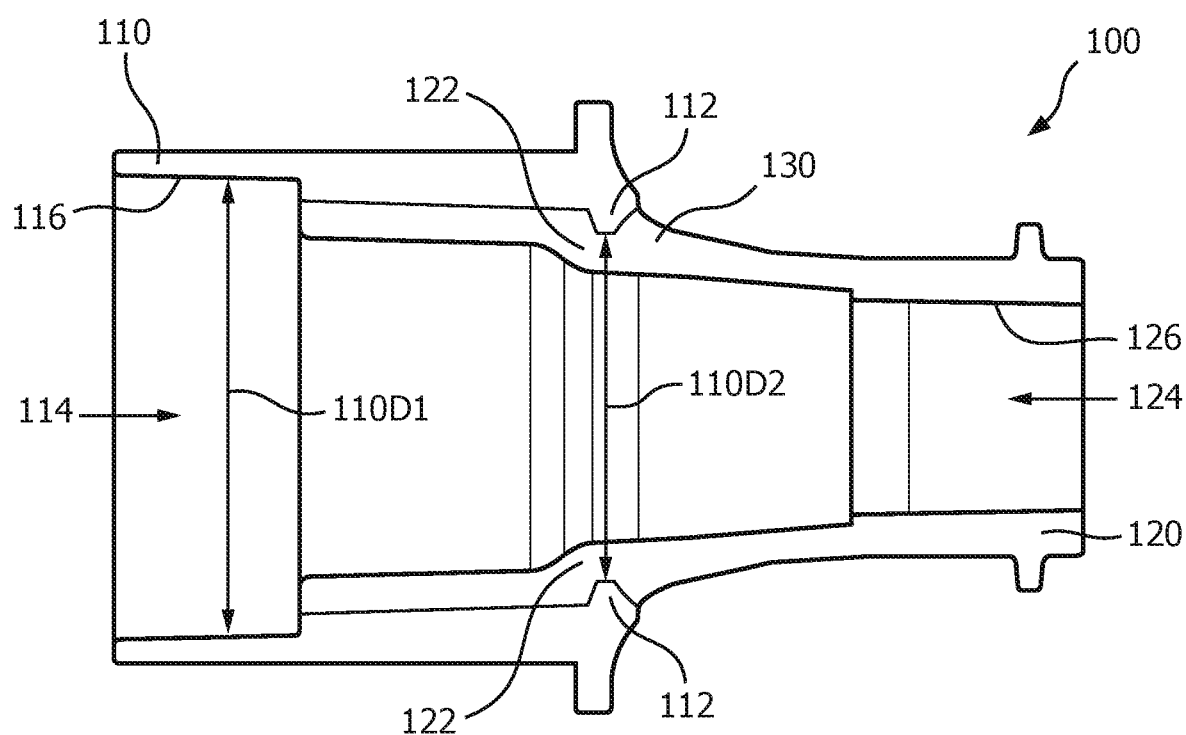
FIGS. 6 and 7 are schematic illustrations of a side cross-sectional view and a side-isometric cross-sectional view, respectively, of the swivel feature of FIG. 5 in accordance with various embodiments.
Figure 7:
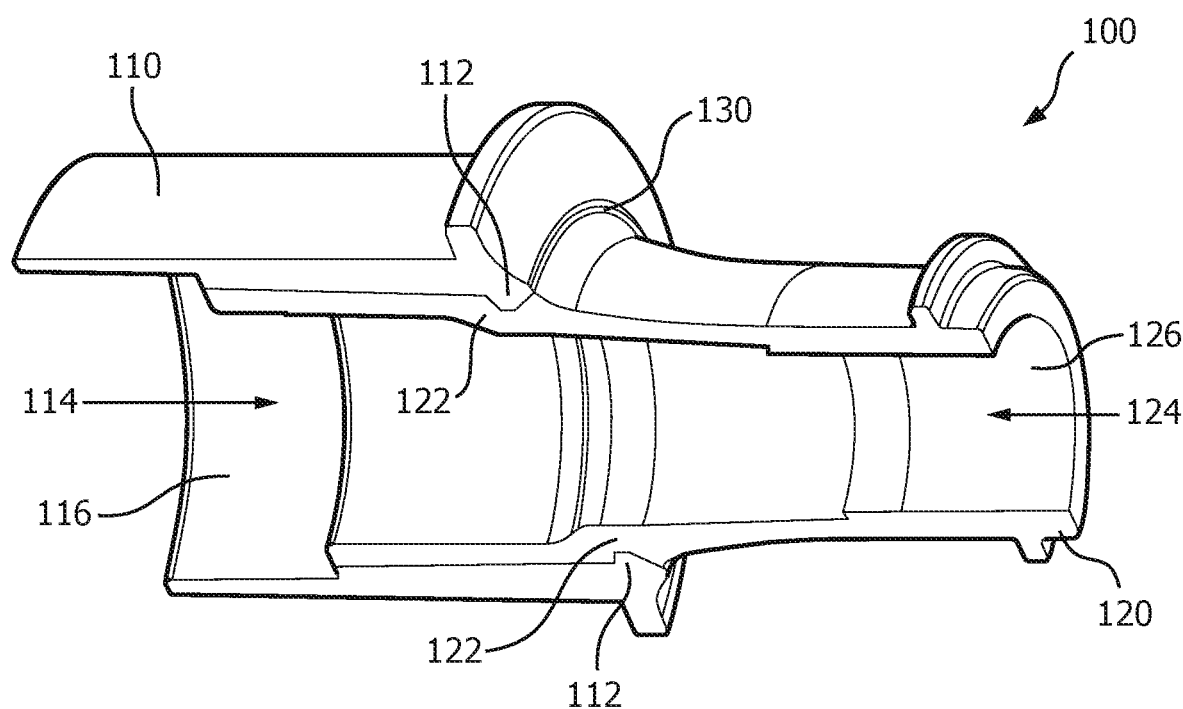

FIG. 5 is a schematic illustration of a side view of a swivel feature 100 in accordance with various embodiments. FIGS. 6 and 7 are schematic illustrations of a side cross-sectional view and a side-isometric cross-sectional view, respectively, of swivel feature 100 of FIG. 5 in accordance with various embodiments. Swivel feature 100 includes an outer swivel component 110, which, in the illustrated exemplary embodiment, is annular about a longitudinal axis, and has an inner surface 116. Outer swivel component 110 is formed, in one embodiment, of a plastic having a low shrink rate, such as a polycarbonate. Outer swivel component 110 includes an angular interlock protrusion 112, which, like outer swivel component 110, is annular about inner surface 116, and extends outwards from inner surface 116 of outer swivel component 110 along a radial axis. In one embodiment, outer swivel component 110 has two or more inner diameters, creating a stepped design. For example, an end 114 of outer swivel component 110 may have a first diameter 110D1, and a first component may be inserted therein (such as, for example and without limitation, a flange or an outlet port of presser generating device 4 of FIG. 4). Another end of outer swivel component 110 opposite end 114 may have a second diameter 110D2, and an inner swivel component 120 may be formed using injection molding techniques at this end of outer swivel component 110. However, for illustrative purposes only, swivel feature 100 is shown without any additional component inserted within outer swivel component 110.

Angular interlock protrusion 112, in one embodiment, has an angular design. As described in detail below, angular interlock protrusion 112, in the illustrated exemplary embodiment, has one side at a first angle and a second side at a second angle, which both meet at a common base and are substantially constant about the annular interior of outer swivel component 110. In one embodiment, the first and second angle are substantially the same, however persons of ordinary skill in the art will recognize that the first and second angles may differ. For example, the first angle may be 105-degrees whereas the second angle may be 135-degrees degrees, however these values are merely exemplary.

Swivel feature 100 also includes inner swivel component 120, which, in the illustrated exemplary embodiment, is formed using injection molding techniques. As described below in greater detail, a plastic, such as polypropylene, which has a high shrink rate, is injected into outer swivel component 110. After sufficient time elapses so that the injected material may cool, inner swivel component 120 is formed. Inner swivel component 120, is substantially annular in shape and has an inner surface 126. At one end of inner swivel component 120 is opening 124, which is opposite end 114, and propagates along a longitudinal axis of swivel feature 100. Opening 124 may be fluidly coupled to delivery conduit 6 so that gas may be delivered from pressure generating device 4 to patient interface 8 through swivel feature 100.

In the exemplary embodiment, inner swivel component 120 includes interlock receiving portion 122, which, after inner swivel component 120 is formed, fits around angular interlock protrusion 112 of outer swivel component 110. In one embodiment, a small clearance is formed between angular interlock protrusion 112 and interlock receiving portion 122 such that inner swivel component 120 may swivel and/or rotate about a swivel hinge 130. Swivel hinge 130 is also annular, and runs along the entirety of swivel feature 100.

In one embodiment, outer swivel component 110 is made of a first material having a shrink rate of less than 0.010 inches per inch, and inner swivel component 120 is made of a second material having a shrink rate greater than 0.012 inches per inch. The first material may be a first plastic and the second material may be a second plastic where the first plastic has a greater melt temperature than the second plastic, and the second plastic has a shrink rate greater than 0.010 inches per inch. In this particular scenario, the first plastic should not continue to shrink once the second plastic is shot inside of it as the first plastic has a great enough melt temperature and shrink rate such that it does not shrink.

In one exemplary embodiment, outer swivel component 110 is made of an amorphous or semi-crystalline material and inner swivel component 120 is made of a semi-crystalline material. The semi-crystalline material used to make outer swivel component 110 may be the same as the semi-crystalline material used to make inner swivel component 120, however, this is merely exemplary, and the two semi-crystalline materials may differ.

Figure 3:
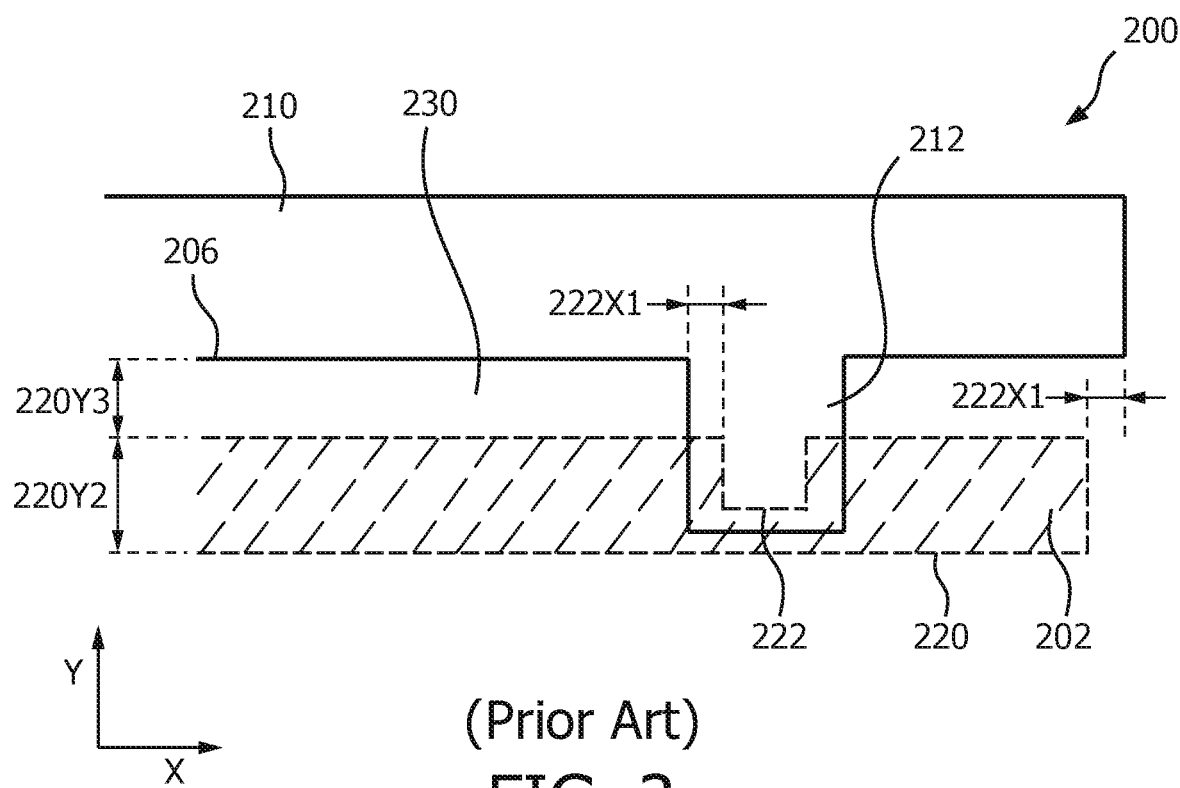
FIG. 3 is a schematic illustration of a cross-sectional side view of a portion of the outer swivel component of FIG. 2 after the inner swivel component material has cooled and shrunk.
Figure 8:
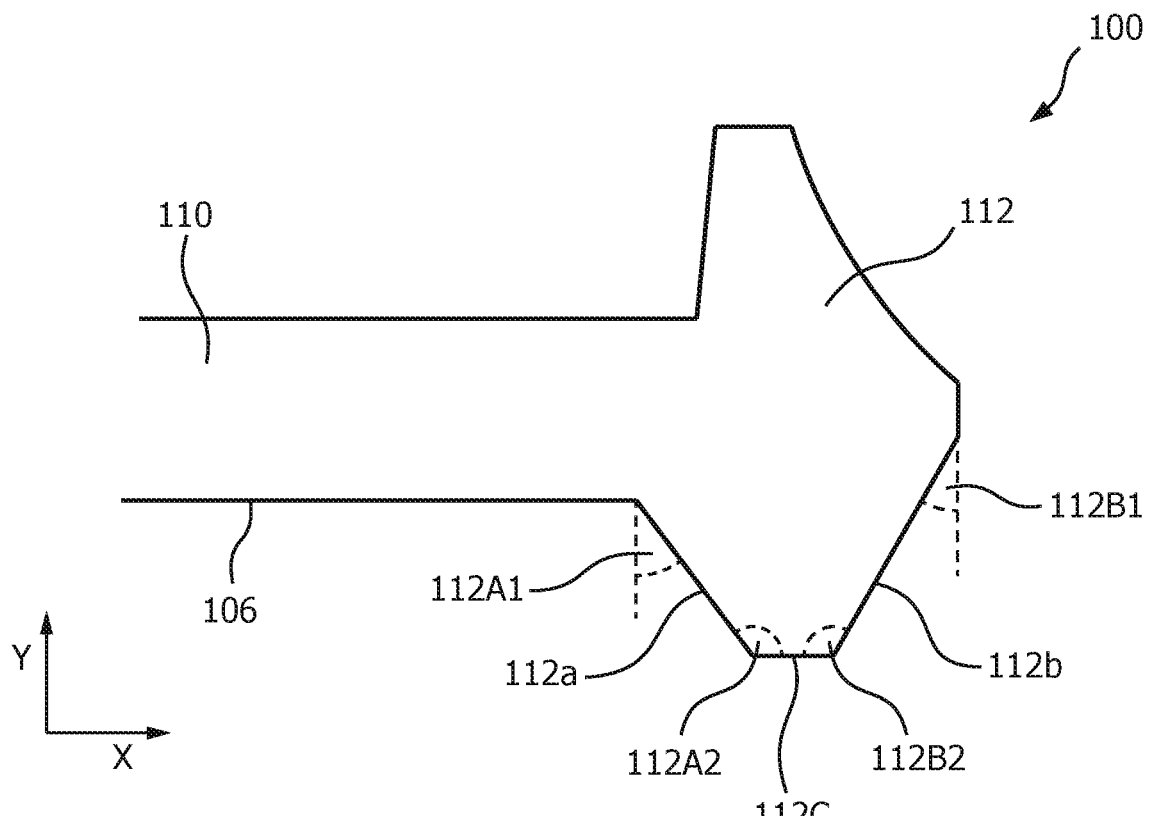
FIG. 8 is a schematic illustration of a top side view of an outer swivel component of the swivel feature having an angular interlock protrusion in accordance with various embodiments.

One way to overcome the interference issue resulting from rectangular interlock protrusion 212 of FIG. 3 is to have an angular interlock protrusion. FIG. 8 is a schematic illustration of a top side view of an outer swivel component 110 of a swivel feature 100 having an angular interlock protrusion 112 in accordance with various embodiments. In the illustrated embodiment, angular interlock protrusion 112 extends outwards along the y-axes (or radial axis) from an inner surface 106 of outer swivel component 110.

Angular interlock protrusion 112 has two angled sides and a horizontal base 112c that is substantially parallel to inner surface 106 of outer swivel component 110. For example, a side 112a of angular interlock protrusion 112 makes an angle 112A1 with the normal of inner surface 106 of outer swivel component 110. As another example, a side 112b of angular interlock protrusion 112 makes an angle 112B1 with the normal of inner surface 106 of outer swivel component 110. Angles 112A1 and 112B1 of sides 112a and 112b of angular interlock protrusion 112 are substantially equal, however in one embodiment, the angles 112A1 and 112B1 are different. For simplicity, swivel feature 100 of FIG. 8 is shown with outer swivel component 110 having angular interlock protrusion 112 with two equal angles for both sides.

An angle 112A2 is equal to angle 112A1 plus 90-degrees, and an angle 112B2 is equal to angle 112B1 plus 90-degrees. In one exemplary embodiment, angle 112A2 is greater than 105-degrees. For example, in order for there to be no interference (e.g., an interface along the x-axis, or the longitudinal axis, shown in FIG. 6), angle 112A2 and angle 112B2 should be greater than 105-degrees. In the illustrated embodiment, angles 112A1 and 112B1, and therefore 112A2 and 112B2, are equal to one another. However, persons of ordinary skill in the art will recognize that angles 112A1 and 112B1 (and thus angles 112A2 and 112B2), may differ from one another. For example, angle 112A2 may be equal to 135-degrees, whereas angle 112B2 may be equal to 110-degrees.

Figure 2:
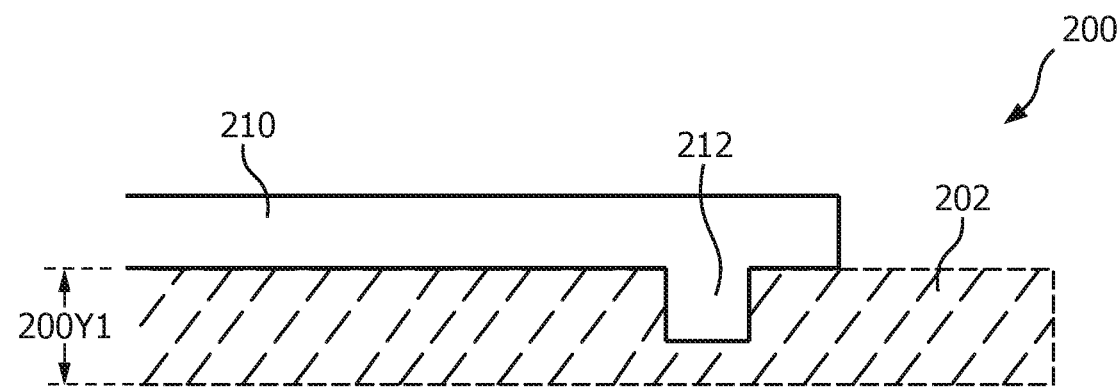
FIG. 2 is a schematic illustration of a side view of the outer swivel component of FIG. 1 having an inner swivel component material injected therein in accordance with an injection molding process.
Figure 2:
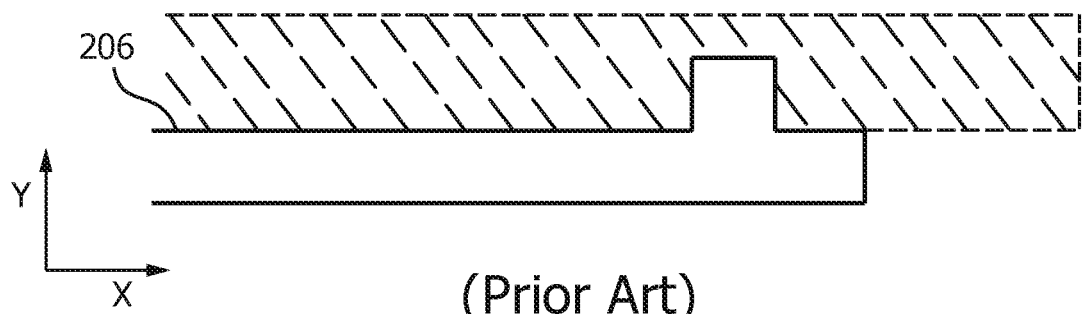
Figure 9:
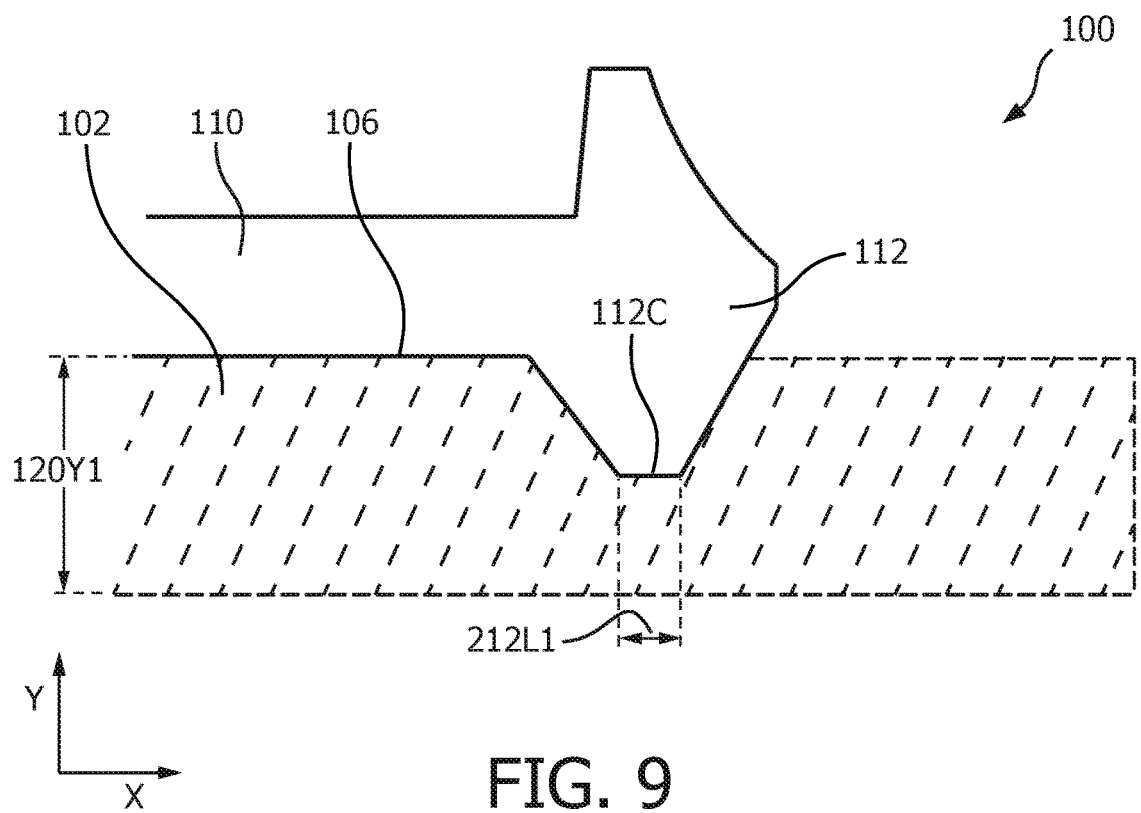
FIG. 9 is a schematic illustration of a top side view of the outer swivel component of FIG. 8 having an inner swivel component material injected therein in accordance with various embodiments

FIG. 9 is a schematic illustration of a top side view of outer swivel component 110 having an inner swivel component material 102 injected therein in accordance with various embodiments. Inner swivel component material 102 is injected within a cavity of outer swivel component 110 in a similar fashion as that of inner swivel component material 202 of FIG. 2, and the previous description may apply. In the illustrated exemplary embodiment, inner swivel component material 102 fills the cavity defined by an inner surface 106 of outer swivel component 110. Inner swivel component material 102 will "extend" out from inner surface 106 of outer swivel component 110 by a distance 120Y1 prior to cooling. Inner swivel component material 102 will also have a width about base 112c of angular interlock protrusion 112 of a distance 112L1. As there is no shrinkage prior to cooling of inner swivel component material 102, distance 112L1 is the starting, or pre-shrunk, length of a receiving portion 122 of inner swivel component 120. Distance 112L1 determines, based on the shrink rate of inner swivel component material 102, an amount of shrinkage 112X2 and an amount of clearance 112X1 along the longitudinal axis, or the x-axis, for inner swivel component 120.

Initially, inner swivel component material 110 is injected at a suitable temperature such that cooling does not occur. For example, inner swivel component material 110 may be injected at a temperature between 100 and 400-degrees Fahrenheit. In one exemplary embodiment, inner swivel component material 110 is injected at 350-degrees Fahrenheit.

In the exemplary embodiment, inner swivel component material 102 is polypropylene. However, persons of ordinary skill in the art will recognize that other materials may be used instead, so long as the injected material has a lower shrinkage temperature and a higher shrinkage rate than the material used to form outer swivel component 110. For example, outer swivel component 110 may be a polycarbonate and may have a substantially low shrink rate, such as 0.0001 inches per inch. In this exemplary embodiment, polypropylene, which inner swivel component material 102 is made of, has a substantially higher shrink rate, such as 0.02 inches per inch, than that of polycarbonate, whose shrink rate is approximately 0.0001 inches per inch.

Figure 10:
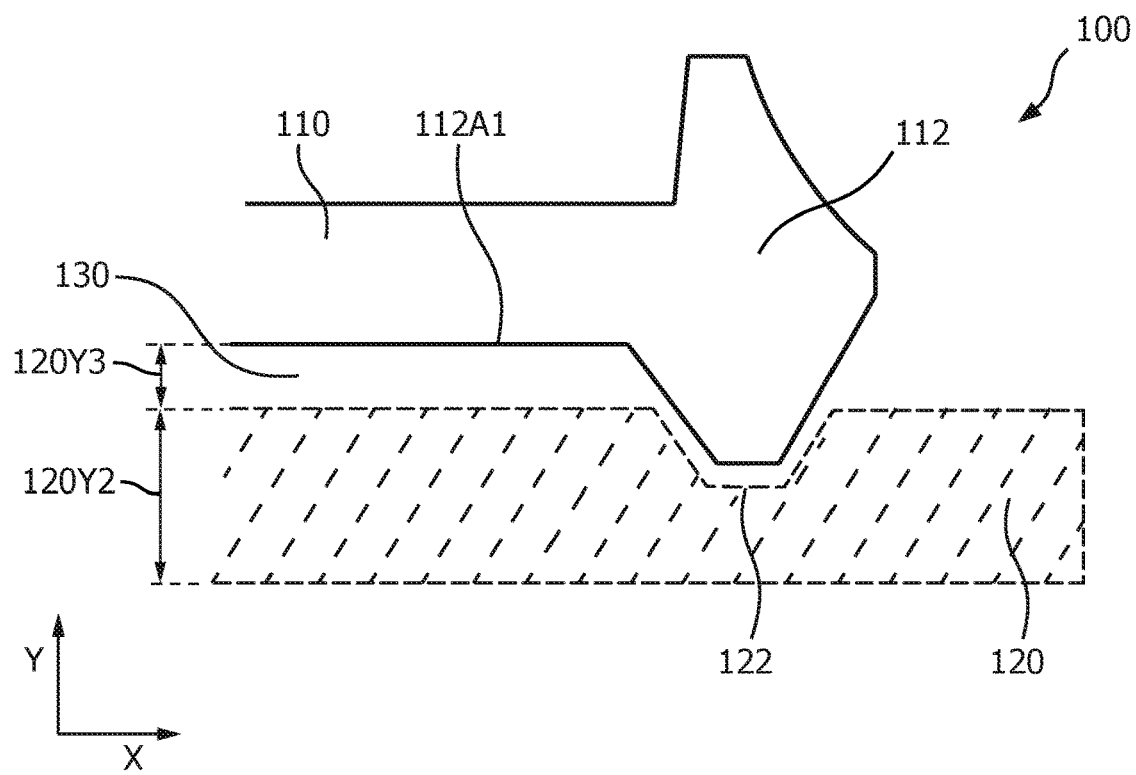
FIG. 10 is a schematic illustration of a top side view of the swivel feature of FIG. 9 after the inner swivel component material has cooled to form an inner swivel component in accordance with various embodiments.

FIG. 10 is a schematic illustration of a top side view of swivel feature 100 after inner swivel component material 102 has cooled to form an inner swivel component 120 in accordance with various embodiments. After a sufficient period of time has passed to allow inner swivel component material 102 of FIG. 8 to cool and form inner swivel component 120, inner swivel component material 102 shrinks in both the x and y directions (or along the longitudinal and radial axes, respectively). In the illustrated embodiment, inner swivel component material 102 shrinks by a distance 120Y3 away from inner surface 106 of outer swivel component 110. Thus, inner swivel component 120 has a thickness 120Y2 in the y-axis, which is smaller than thickness 120Y1 of inner swivel component material 102 prior to cooling. By shrinking away from inner surface 106 of outer swivel component 110, a clearance 130 in the y-direction, or radial direction, between an outer surface 126 of swivel component 120 and inner surface 106 of outer swivel component 110 is created.

Furthermore, prior to being cooled, inner swivel component material 102 directly abuts angular interlock portion 112. As inner swivel component material 102 cools, it also shrinks along the x-axis creating a clearance around angular interlock protrusion 112. This clearance is not attainable with rectangular interlock portion 212 of FIG. 5, as the shrinkage in the x-direction will cause an interference to form about rectangular interlock protrusion 212. In the illustrated exemplary embodiment, inner swivel component material 102 will shrink by an amount 112X2 in the x-direction. This amount of shrinkage, 112X2, in the x-direction will allow for a clearance distance 112X1 to be created between sides 112a and 112b of angular interlock protrusion 112, thereby enabling swivel feature 100 to rotate properly.

Figure 11:
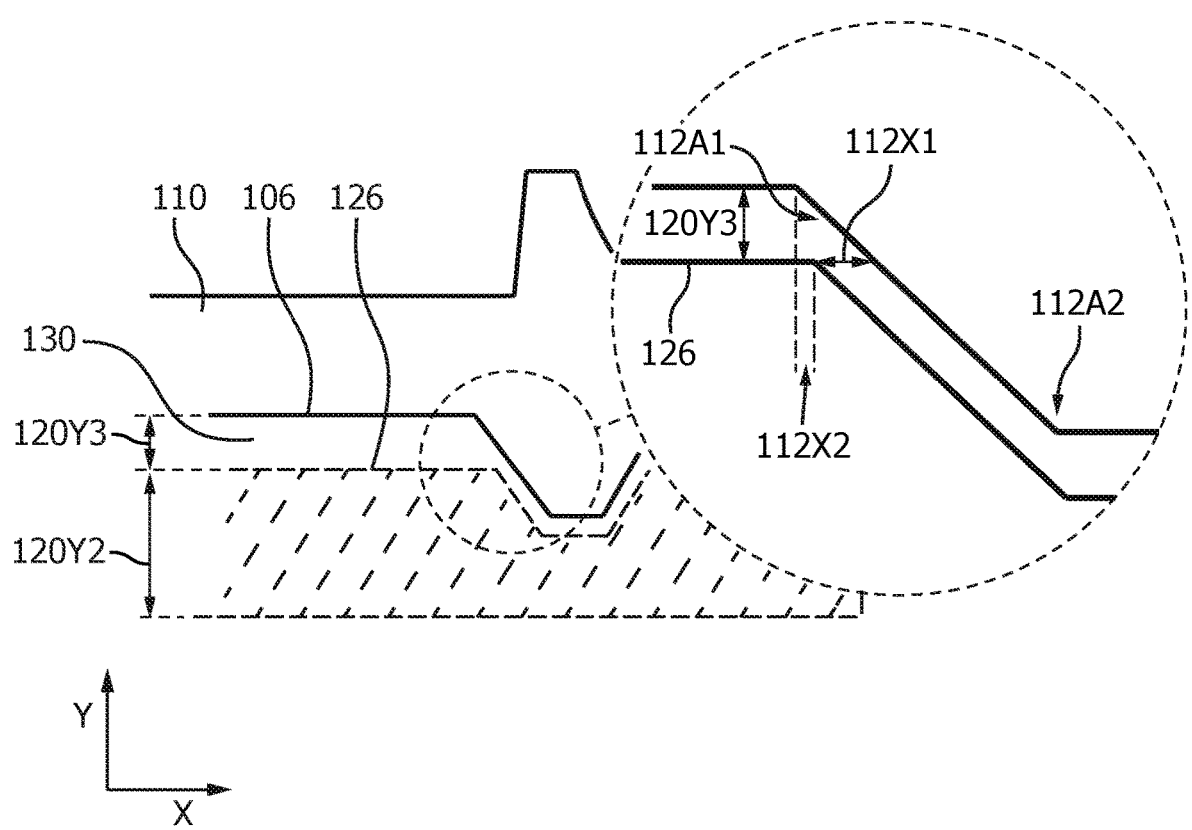
FIG. 11 is a schematic illustration of a zoomed in portion of the clearance formed by the angular interlock protrusion of FIG. 10 in accordance with various embodiments.

FIG. 11 is a schematic illustration of a zoomed in portion of the clearance formed by angular interlock protrusion 112 of FIG. 10 in accordance with various embodiments. As inner swivel component material 102 shrinks, as it cools, clearance 130 is formed between inner swivel component 120 and outer swivel component 110. This distance 120Y3 corresponds to the amount of clearance obtained along the y-axis due to shrinkage of the material along the y-axis. For example, if inner swivel component material 102 has a shrinkage rate of 0.02 inches per inch, then if the starting distance 120Y1 was 1 inch, the final width 120Y2 of inner swivel component 120 would be 0.98 inches, making clearance distance 120Y3 0.02 inches.

Furthermore, as inner swivel component material 102 cools, it also shrinks along the x-axis. For example, for each side of angular interlock protrusion 112, shrinkage amount 112X2 is equal to half of the product of distance 112L1 and the shrinkage rate for inner swivel component material 102. For example, if distance 112L1 is 1 inch, and the shrinkage rate of inner swivel component material 102 is 0.02 inches per inch, then distance 112X2 will be (1 inch×0.02 inches per inch)/2, which equals 0.01 inches.

Clearance 112X1, which is calculated based on the shrinkage along the x-axis and the y-axis, equals:

$$112X1 = (120Y3 \times \tan 112A1) - \frac{1}{2}112X2.$$

Thus, the total clearance, taking into account both sides 112a and 112b of angular interlock protrusion 112, is double the amount of clearance 112X1, so long as angles 112A1 and 112B1 are equal. Persons of ordinary skill in the art, however, will recognize that if angles 112A1 and 112B1 are not equal, then the total clearance will not be twice the amount of 112X1, and separate calculations are required for both sides.

By using angular interlock protrusion 112, the interference that would normally occur if a rectangular interlock is used, is now eliminated. This will allow inner swivel component 120 to properly swivel within outer swivel component 110 with minimal binding and provides a much more effective and solid conduit for a patient. Furthermore, by creating swivel feature 100 using a two-shot molding technique, swivel 100 is now able to be created as one, without having to create an inner swivel component and an outer swivel component and then connecting the two together. This eliminates an entire step of production, save valuable manufacturing time. Additionally, as both inner swivel component 120 and outer swivel component 110 are formed together, uniformity between components is now possible. Two separate components do not have to be connected, and each swivel feature 100 is now formed as one unit, increasing cost-saving and quality.

It can thus be appreciated that the present invention provides a conduit having a swivel feature formed using injection molding techniques, in particular overmolding techniques, that maintains the rotational capabilities of the swivel feature while also minimizing leakage.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A swivel feature for a conduit between a pressure generating device delivering breathing therapy to a patient and a patient interface device donned by the patient, the swivel feature comprising:
    an outer swivel component having an annular cross-section and comprising an angular interlock protrusion extending radially inward from an inner surface of the outer swivel component, wherein the angular interlock protrusion has a first angled side extending in a straight manner from the inner surface of the outer swivel component at a first non-zero angle from a normal to the inner surface, a second angled side extending in a straight manner from the inner surface of the outer swivel component at a second non-zero angle from the normal to the inner surface, and a flat horizontal base extending between the first angled side and the second angled side, wherein the flat horizontal base extends parallel to the inner surface of the outer swivel component; and
    an inner swivel component having an annular cross-section and comprising an angular interlock receiving portion which allows the angular interlock protrusion to extend therein, the swivel feature further comprising:
        a first clearance distance along a radial axis between an outer surface of the inner swivel component and the inner surface of the outer swivel component; and
        a second clearance distance along a longitudinal axis between both the first and second angled sides of the angular interlock protrusion and the angular interlock receiving portion, wherein the first clearance distance is greater than the second clearance distance.

2. The swivel feature of claim 1, wherein the angular interlock receiving portion is formed after an inner swivel component material is injected into the outer swivel component and allowed to cool for a period of time.

3. The swivel feature of claim 1, wherein the outer swivel component comprises polycarbonate, and the inner swivel component comprises polypropylene.

4. The swivel feature of claim 1, wherein the outer swivel component is made out of a material having a first shrink rate, wherein the inner swivel component is made out of a material having a second shrink rate, and wherein the second shrink rate is greater than the first shrink rate.

5. The swivel feature of claim 4, wherein the first shrink rate is less than 0.010 inches per inch, and wherein the second shrink rate is greater than 0.012 inches per inch.

6. The swivel feature of claim 4, wherein the material having the first shrink rate is a first plastic, wherein the material having the second shrink rate is a second plastic, wherein the first plastic has a melt temperature that is greater than the second plastic, and wherein the second plastic has a shrink rate that is greater than 0.010 inches per inch.

7. The swivel feature of claim 4, wherein the second shrink rate of the inner swivel component is the same along the radial axis of the inner swivel component and the longitudinal axis of the inner swivel component.

8. The swivel feature of claim 1, wherein the outer swivel component is made of one of: an amorphous material and a first semi-crystalline material, wherein the inner swivel component is made of a second semi-crystalline material, and wherein the one of amorphous material and the first semicrystalline material has a higher melt temperature than the second semi-crystalline material.

9. The swivel feature of claim 1, wherein the first clearance distance along the radial axis is constant along the longitudinal axis of the swivel about either side of the angular interlock protrusion.

10. The swivel feature of claim 1, wherein the first non-zero angle and the second non-zero angle are one of: the same; and different.

11. The swivel feature of claim 1, wherein the first non-zero angle and the second non-zero angle are at least 10-degrees.

12. The swivel feature of claim 1, wherein the inner swivel component is formed by injecting an inner swivel component material into a cavity formed by the inner surface of the outer swivel component.

13. The swivel feature of claim 12, wherein, when injected, the inner swivel component material initially has a temperature between 100 and 400-degrees Fahrenheit.

14. The swivel feature of claim 12, wherein, after a period of time, the inner swivel component material shrinks by the first clearance distance along the radial axis and the second clearance distance along the longitudinal axis to form the inner swivel component.

15. The swivel feature of claim 14, wherein the period of time is between 10 seconds and 2 minutes.

16. The swivel feature of claim 14, wherein after the period of time, the inner swivel component is formed and has a width along the radial axis.

17. The swivel feature of claim 1, wherein the outer swivel component is molded first and then an inner swivel component material is injected into the outer swivel component to create the inner swivel component.

18. A gas delivery system for delivering a breathing gas to a patient comprising the swivel feature, the pressure generating device, and the patient interface device of claim 1 wherein the swivel feature is fluidly coupled to the pressure generating device and the patient interface device.

19. A patient circuit for delivering a breathing gas to a patient comprising the swivel feature and the patient interface device of claim 1, wherein the swivel feature is fluidly coupled to the patient interface device.

20. The swivel feature of claim 1, wherein the first clearance distance is double the second clearance distance.

21. The swivel feature of claim 1, wherein the second angled side is longer than the first angled side.

\* \* \* \* \*